United States Patent
Hayakawa et al.

(10) Patent No.: US 6,623,424 B2
(45) Date of Patent: Sep. 23, 2003

(54) FLEXIBLE TUBE FOR AN ENDOSCOPE AND ELECTRONIC ENDOSCOPE EQUIPPED WITH THE FLEXIBLE TUBE

(75) Inventors: Shinji Hayakawa, Saitama (JP); Akira Sugiyama, Kanagawa (JP); Masaru Takeshige, Tokyo (JP); Tadashi Kasai, Saitama (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 09/943,205

(22) Filed: Aug. 31, 2001

(65) Prior Publication Data

US 2002/0028984 A1 Mar. 7, 2002

(30) Foreign Application Priority Data

Sep. 1, 2000 (JP) .......................................... 2000-265847

(51) Int. Cl.$^7$ .................................................. A61B 1/00
(52) U.S. Cl. ........................................ 600/139; 600/140
(58) Field of Search .................................. 600/139, 140, 600/121; 604/524, 526, 527

(56) References Cited

U.S. PATENT DOCUMENTS

| | | | | |
|---|---|---|---|---|
| 4,690,175 A | * | 9/1987 | Ouchi et al. | 600/140 |
| 4,753,222 A | * | 6/1988 | Morishita | 600/140 |
| 4,899,787 A | * | 2/1990 | Ouchi et al. | 600/140 |
| 5,217,002 A | * | 6/1993 | Katsurada et al. | 600/139 |
| 5,448,988 A | * | 9/1995 | Watanabe | 600/139 |
| 5,876,331 A | * | 3/1999 | Wu et al. | 600/139 |
| 5,885,207 A | * | 3/1999 | Iwasaka | 600/139 |
| 5,916,147 A | * | 6/1999 | Boury | 600/139 |
| 6,083,152 A | * | 7/2000 | Strong | 600/139 |
| 6,197,014 B1 | * | 3/2001 | Samson et al. | 604/524 |
| 6,206,824 B1 | * | 3/2001 | Ohara et al. | 600/139 |
| 6,402,687 B1 | * | 6/2002 | Ouchi | 600/139 |
| 6,458,075 B1 | * | 10/2002 | Sugiyama et al. | 600/139 |

FOREIGN PATENT DOCUMENTS

JP        6-181882         7/1994

* cited by examiner

Primary Examiner—Linda C. M. Dvorak
Assistant Examiner—Jocelyn Ram
(74) Attorney, Agent, or Firm—Greenblum & Bernstein, P.L.C.

(57) ABSTRACT

A flexible tube for an endoscope which has excellent insertion operability is disclosed. The flexible tube includes and an elongated flexible tubular body constructed from a core body having a hollow space and an outer cover which is provided over the outer periphery of the core body and formed into a laminated structure having a plurality of layers. The tubular body is formed with a plurality of easily bendable portions which are provided in a spaced apart manner along the longitudinal direction thereof, each of these easily bendable portion being adapted to bend locally with a smaller curvature radius when the flexible tube is bent in one direction. The average interval between the adjacent easily bendable portions is preferably in the range 50–400 mm. The easily bendable portions is formed by locally changing the flexural rigidity of the outer cover. For example, it is formed by changing the thickness of at least one layer of the laminated structure of the outer cover at a position corresponding to the easily bendable portion.

16 Claims, 8 Drawing Sheets

FLEXIBLE TUBE FOR AN ENDOSCOPE AND ELECTRONIC ENDOSCOPE EQUIPPED WITH THE FLEXIBLE TUBE

BACKGROUND OF THE INVENTION

1. Field of the Invention

This invention relates to a flexible tube for an endoscope and an electronic endoscope equipped with the flexible tube.

2. Description of the Prior Art

A medical endoscope is used in medical procedures for diagnosing and treating diseases. This type of medical endoscope includes an elongated insertion portion which is to be inserted into a body cavity (tubular cavity). The insertion portion is formed into an elongated tubular shape having a hollow space through which medical instruments such as an optical fiber, electrical cable, mechanical cable, tubes and the like are inserted and arranged. Further, except for the tip portion thereof, the insertion portion is constructed from a flexible tube for an endoscope (hereinafter, simply referred to as "flexible tube" or "flexible insertion tube" depending on occasions) having a prescribed flexibility (elasticity).

The endoscope is used by inserting the insertion portion deep into a body cavity, for example, the stomach, duodenum, small intestine or large intestine. When inserting the insertion portion of the endoscope into the body cavity, the flexible tube (insertion portion) is advanced into the body cavity by applying a push-in force or a twist to the base end (proximal side) of the flexible tube.

However, the flexible tube for an endoscope is quite long and needs to bend along the curves of the body cavity during insertion. Therefore, even when an inserting operation force such as a push-in force and twist is applied thereto, the flexible tube experiences a lot of resistance due to such factors as friction with the inner walls of the body cavity and the like. For this reason, it is not easy to advance the tip portion thereof into the body cavity. Because the operation for inserting the flexible tube into a body cavity is difficult as described above, there has been a need for a flexible tube that can be more easily inserted into a body cavity.

SUMMARY OF THE INVENTION

It is an object of the present invention to provide a flexible tube for an endoscope that has excellent operability so as to be easily inserted into a body cavity.

In order to achieve the above object, the present invention is directed to a flexible tube for an endoscope which comprises an elongated flexible tubular body and a plurality of easily bendable portions provided in the tubular body in a spaced apart manner along the longitudinal direction thereof. Each of these easily bendable portion is adapted to be bent locally with a smaller curvature radius when the flexible tube is bent in one direction.

According to the flexible tube for an endoscope of the present invention described above, since the resistance that the flexible tube receives from the inner walls of a body cavity when being advanced is reduced, it becomes possible to easily insert the flexible tube for an endoscope deep into the interior of the body cavity. Accordingly, the flexible tube for an endoscope of the present invention has excellent insertion operability.

In a preferred embodiment of the present invention, the average interval between the adjacent easily bendable portions is in the range 50–400 mm. This makes it possible to further improve the insertion operability.

Further, in the preferred embodiment of the present invention, when the average of the curvature radius of each of said easily bendable portions is defined as $R_1$ and the curvature radius of the center portion lying between said adjacent easily bendable portions is defined as $R_2$, the value of the ratio $R_1/R_2$ in the bending state lies in the range of 0.2–0.9. This also improves the insertion operability.

In the present invention, the flexible tubular body is preferably constructed from a core body having a hollow space and an ouster cover which is provided over the outer periphery of the core body, and the outer cover being formed into either of a single layer structure or a laminated structure having a plurality of layers.

In this case, it is preferred that each of said easily bendable portions is formed by locally changing the flexural rigidity of the outer cover. This makes it possible to realize a flexible tube for an endoscope having excellent insertion operability with a simple structure which can be easily manufactured.

Further, in the preferred embodiment, at least one of said easily bendable portions is formed by changing the thickness of at least one layer of the laminated structure of the outer cover at a position corresponding to the easily bendable portion. According to this, it is possible to form the easily bendable portions easily.

Alternatively, in the preferred embodiment, at least one of said easily bendable portions may be constructed from a portion of the outer cover where the thickness of the outer cover changes along the circumferential direction. This also makes it possible to form the easily bendable portions easily.

In the present invention, it is preferred that the outer cover has a portion which is made of a material including at least one kind of material selected from the group consisting of polyurethane-based elastomer, polyester-based elastomer, polyolefin-based elastomer, polystyrene-based elastomer, polyamide-based elastomer, and fluoro-based elastomer. Use of such a material makes it possible to improve characteristics required for a flexible tube for an endoscope.

Preferably, the outer cover is applied over the core body using an extrusion molding method. This makes it possible to manufacture the flexible tube with high productivity.

Further, preferably, the core body includes a coil formed by winding a band-shaped material into a spiral and a braided tube provided over the outer periphery of the coil and formed by braiding fine wires. This makes it possible to have sufficient mechanical strength.

In another preferred embodiment of the present invention, at least one of said easily bendable portions is formed by forming the outer cover so as to have an elliptical cross section at a position corresponding to the easily bendable portion.

Further, in other preferred embodiment of the present invention, at least one of said easily bendable portions can be formed by increasing the winding pitch of the coil locally at a position corresponding to the easily bendable portion. Furthermore, at least one of said easily bendable portions may be formed by reducing the width and/or thickness of the band-shaped material of the coil 21 locally at a position corresponding to the easily bendable portion.

Another aspect of the present invention is directed to an electronic endoscope which comprises an operation section which is operated by an operator and a flexible tube for an endoscope which is connected to the operation section. The flexible tube includes an elongated flexible tubular body and a plurality of easily bendable portions provided in the tubular body in a spaced apart manner along the longitudinal direction thereof. Each of these easily bendable portion is adapted to bend locally with a smaller curvature radius when the flexible tube is bent in one direction.

These and other objects, structures and results of the present invention will be apparent more clearly when the following detailed description of the preferred embodiments is considered taken in conjunction with the accompanying drawings.

DETAILED DESCRIPTION OF THE INVENTION

With reference to the appended drawings, a detailed description of the preferred embodiments of a flexible tube for an endoscope according to the present invention will now be given below.

Figure 1:
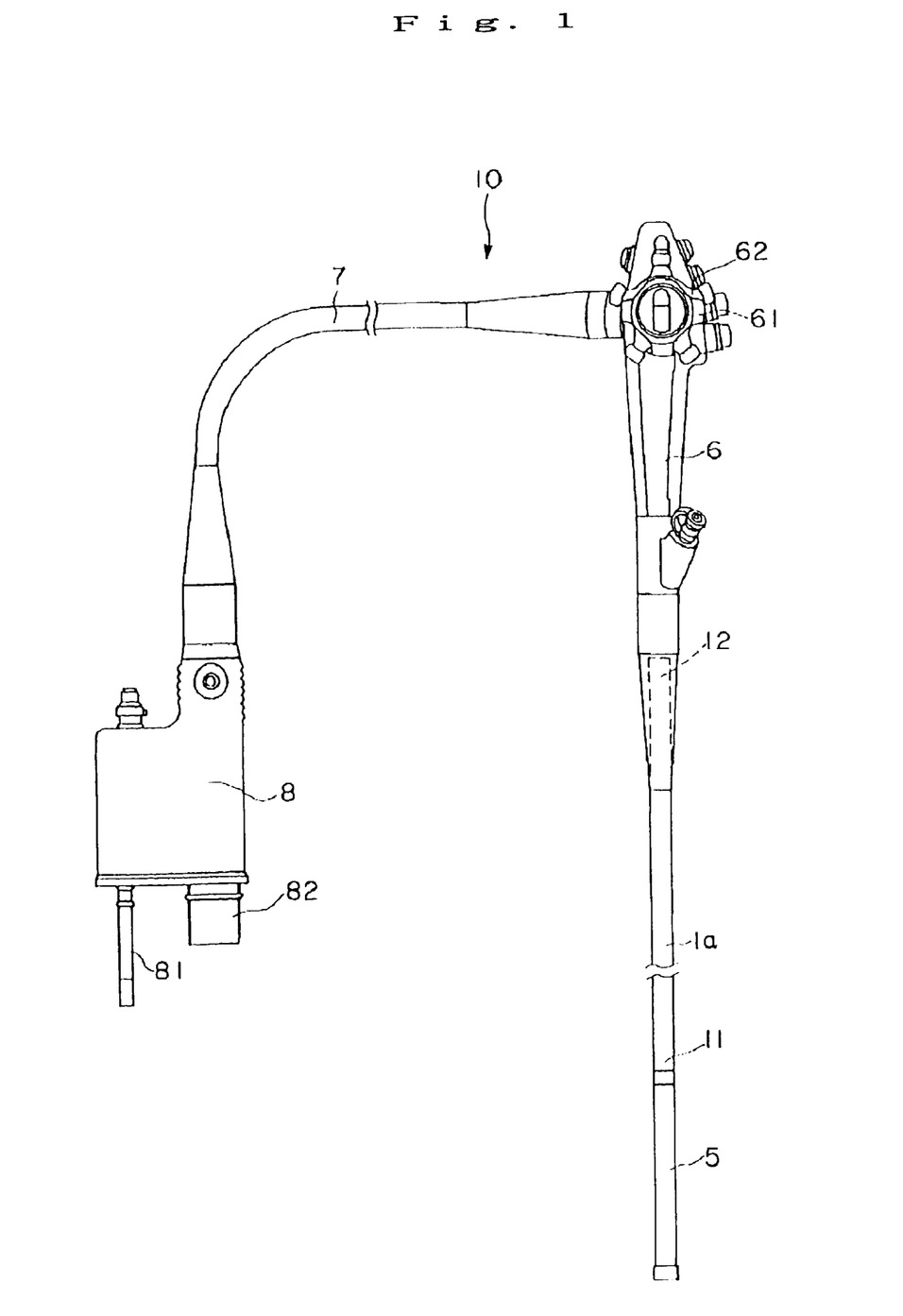
FIG. 1 is an overall view showing an electronic endoscope which includes a flexible tube for an endoscope in accordance with the present invention.

FIG. 1 is an overall view showing an electronic endoscope (electronic scope) which includes a flexible tube for an endoscope manufactured in accordance with the present invention. A description will now be given for the overall structure of the electronic endoscope 10 shown in FIG. 1. In this regard, the upper side in FIG. 1 will be referred to as the "base or proximal" side, and the lower side in FIG. 1 will be referred to as the "tip or distal" side.

Namely, an electronic endoscope 10 has an elongated flexible tube 1a having a prescribed flexibility (elasticity); a bendable tube 5 connected to a tip end 11 of the flexible tube 1a; an operating section 6 provided on a base end 12 of the flexible tube 1a, which is gripped by an operator during an endoscopic examination to manipulate the entire endoscope 10; a flexible connection tube 7 connected at one end thereof to the operating section 6, and a light source plug section 8 provided on the other end of the flexible connection tube 7.

The flexible tube 1a is adapted for insertion into a tubular cavity of a living body. Further, operation knobs 61, 62 are provided on the side of the operating section 6. When these operation knobs 61, 62 are operated, wires (not shown in the drawing) arranged inside the flexible tube 1a are pulled thereby to force the bendable tube 5 connected to the tip end 11 of the flexible tube 1a to bend in four directions, and in this way the tip end 11 can be made to bend in any direction.

An imaging element (CCD) not shown in the drawings is provided in the tip end portion of the bendable tube 5 to take observation images of the observation region inside the body cavity, and an image signal connector 82 is provided at the tip end portion of the light source plug section 8. The image signal connector 82 is connected to a light source processor device (not shown in the drawing) which is in turn connected to a monitor device (not shown in the drawing) via a cable.

Further, a light source connector 81 is provided at the tip end portion of the light source plug section 8, and this light source connector 81 is connected to the light source processor device. The light emitted from the light source inside the light source processor device passes through the light source connector 81 and a light guide (not shown in the drawings) comprised of an optical fiber bundle that runs through the inside of the light source plug section 8, the inside of the flexible connection tube 7, the inside of the operating section 6, the inside of the flexible tube 1a and the inside of the bendable tube 5, and the light that is irradiated from the tip end portion of the bendable tube 5 illuminates the observation region.

The reflected light (observation images) from the observation region illuminated by the illumination light is picked up by the imaging element. Then, image signals corresponding to the observation images taken by the imaging element are outputted via a buffer (not shown in the drawing).

These image signals are transmitted to the light source plug 8 via an image signal cable (not shown in the drawings) which extends inside the bendable tube 5, the flexible tube 1a, the operating section 6, and the flexible connection tube 7 in order to connect the imaging element and the image signal connector 82.

Then, after a prescribed processing (e.g., a signal process, image process, etc.) is carried out in the light source plug section 8 and light source processor device, the image signals are inputted into a monitor device. In the monitor device, the images (electronic images) taken by the imaging element are displayed. Namely, moving images are displayed on the endoscope monitor.

Figure 2:
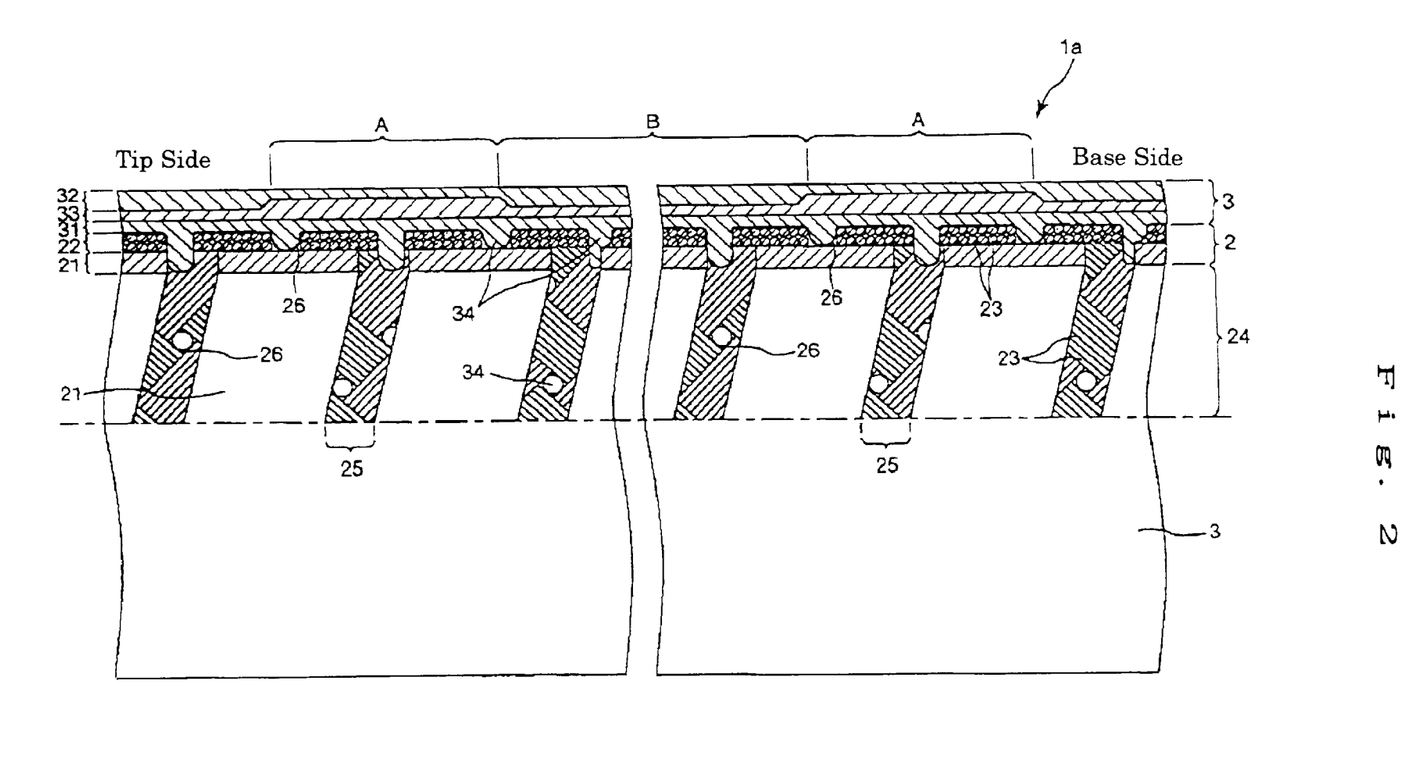
FIG. 2 is a partially cross-sectional view showing a first embodiment of a flexible tube for an endoscope in accordance with the present invention.
Figure 3:
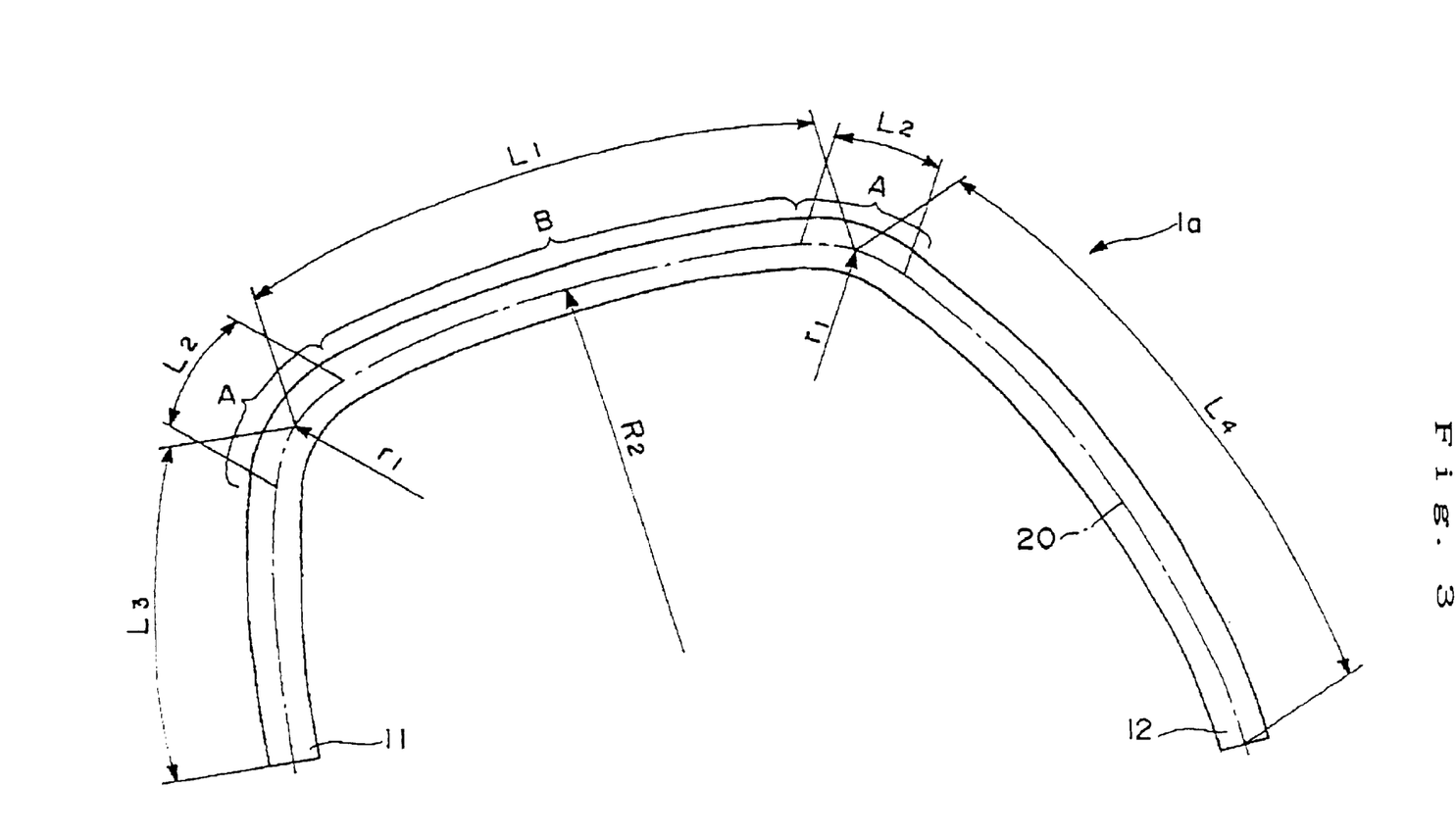
FIG. 3 is an illustration showing the state that the flexible tube shown in FIG. 2 is being bent.
Figure 4:
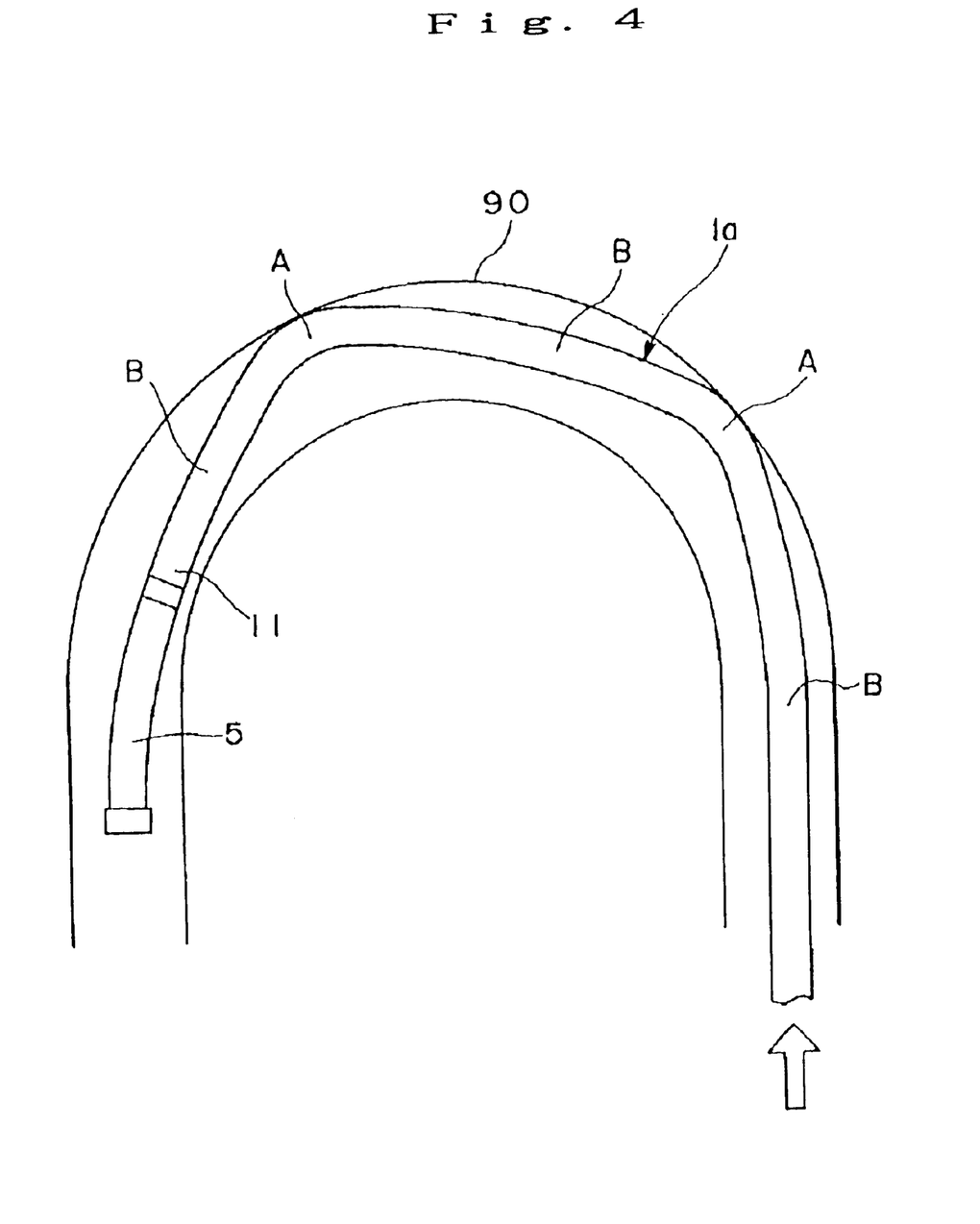
FIG. 4 is an illustration showing the state that the flexible tube shown in FIG. 2 is inserted into a body cavity.

In the above, the description was given for the overall structure of the endoscope to which the flexible tube for an endoscope according to the present invention is applied. However, the present invention is not limited to this application, and it is possible for the flexible tube for an endoscope of the present invention to be applied as a flexible tube for other types of scopes, such as a flexible tube for a fiber scope Next, FIG. 2 is a partially cross-sectional view showing a first embodiment of a flexible tube for an endoscope in accordance with the present invention; FIG. 3 is an illustration showing the state that the flexible tube shown in FIG. 2 is being bent; and FIG. 4 is an illustration showing the state that the flexible tube shown in FIG. 2 is inserted into a body cavity. In FIG. 2, the left side will be referred to as a tip side (distal side) 11, and the right side will be referred to as a base side (proximal side) 12.

As shown in FIG. 2, the flexible tube 1a includes a core body 2 and an outer cover 3 which covers the outer periphery of the core body 2. Further, a hollow space 24 is provided inside the flexible tube 1a to enable various instruments (omitted from the drawings) such as an optical fiber, electrical cable, mechanical cable, tubes and the like to be passed therethrough and arranged therein.

The core body 2 is constructed from a coil 21 and a reticular tube (braided tube) 22 which covers the outer periphery of the coil 21 to form an elongated tubular body. One function of this core body 2 is to reinforce the flexible tube 1a. Namely, by combining the coil 21 and the reticular tube 22, it is possible to ensure that the flexible tube 1a is given sufficient mechanical strength. Further, although it is not shown in the drawings, it is possible to obtain even higher strength by providing two or three layers of the coil 21.

The coil 21 is formed by winding a band-shaped material into a spiral having a uniform diameter and prescribed gaps 25. Preferably, a metal such as stainless steel, copper alloy or the like is used to make such band-shaped material.

The reticular tube 22 is formed by braiding a plurality of metal or nonmetal fine wires 23 into a tubular lattice structure. The fine wires 23 are preferably made of stainless steel, copper alloy or the like. Further, at least one of the fine wires used to construct the reticular tube 22 may be covered with a synthetic resin (not shown in the drawings).

The reticular tube 22 has many spaces comprised of the stitches of the braided fine wires 23. These spaces 26 are in the form of concave portions at the positions that overlap with the outer periphery of the coil 21, and in the form of holes extending to the hollow spaces 24 at the positions which overlap with the gaps 25 of the coil 21. Therefore, a plurality of holes and concave portions are formed in the outer periphery of the core body 2.

The outer periphery of the core body 2 is covered with the outer cover 3. The outer cover 3 is formed into a laminated body (laminated structure) which includes an inner layer 31, an outer layer 32 and an intermediate layer 33.

As described below, each layer any one of the inner layer 31, outer layer 32 and intermediate layer 33 of the outer cover 3 is made of a material having different physical and chemical properties than any one of the other layers. Examples of physical properties include stiffness (flexibility), hardness, elongation percentage, tensile strength, shear strength, flexural elasticity, bending strength and the like, and examples of chemical properties include chemical resistance, weather resistance and the like. In this regard, it should be noted that the present invention is not limited to these examples, and it is of course possible to include any properties.

The inner layer 31 is formed at the innermost peripheral side of the outer cover 3 and is bonded to the core body 2.

A plurality of protruding portions (anchors) 34 which protrude toward the inside are formed on the inner peripheral surface of the inner layer 31 so as to be integral portions that extend inward from the inner layer 31. These protruding portions 34 extend into the plurality of holes and concave portions formed in the core body 2. The tips of the protruding members 34 that extend inside the concave portions are formed so as to reach the outer periphery of the coil 21. The protruding portions 34 that extend into the holes are formed to be even longer in order for the tips thereof to extend into the gaps 25 of the coil 21.

Further, the inner layer 31 is preferably formed of a material with which the size (length), shape and number of the protruding portions 34 can be controlled appropriately.

As described above, the protruding portions 34 engage with the plurality of holes and concave portions formed in the outer periphery of the core body 2. Therefore, an anchor effect will occur, and this will reliably secure the outer cover 3 to the core body 2. As a result, even in the case where the flexible tube 1 is bent, the outer cover 3 will maintain a bonded state with the core body 2, and will undergo large expansion and contraction to follow the bending of the core body 2. Further, the restoring force of the outer cover 3 undergoing such large expansion and contraction is strong enough to serve as a force for restoring the shape of the bent flexible tube 1. Accordingly, by adopting such structure as described above, the flexible tube 1 can have excellent resilience. Furthermore, because the flexible tube 1a has a high resilience as described above, it will be difficult to be a state that the push-in force applied to the base end portion is absorbed by the bent portion, that is buckling is not liable to occur, and this further improves the insertion operability.

Further, because the formation of the protruding portions 34 makes it possible to create a strong bonding force between the outer cover 3 and the reticular tube 22, the outer cover 3 will be difficult to peel off from the reticular tube 22 even over repeated use. Accordingly, because the flexible tube 1a will maintain excellent resilience even after repeated use, the flexible tube 1a will have excellent durability.

Now, in the case where at least one of the fine wires forming the reticular tube 22 is covered with a synthetic resin, at least a part of this resin cover (coating layer) is melted and bonded (fused) with the inner layer 31. In this case, by forming the inner layer 31 from a constituent material which includes a material having excellent compatibility with the synthetic resin coating layer of the fine wire 23, it becomes possible to sufficiently bond the coating layer of the fine wire 23 to the inner layer 31.

In the case where the coating layer of the fine wire 23 is bonded with the inner layer 31 as described above, the adhesion between the outer cover 3 and the core body 2 is even higher, and the bonding force between the outer cover 3 and the core body 2 is even stronger. Therefore, the flexible tube 1a exhibits excellent resilience and durability in combination with the effect resulted from the formation of the protruding portions 34 described above.

The constituent material of the inner layer 31 is not particularly limited to a specific material. It is possible to use various resins having flexibility such as polyvinyl chloride, polyolefin-based resin (e.g., polyethylene, polypropylene, ethylene-vinylacetate copolymer), polyamide-based resin, polyester-based resin (e.g., polyethylene terephthalate (PET), polybutylene terephthalate), polyurethane-based resin, polystyrene-based resin, fluoro-based resin (e.g., polytetrafluoroethylene, ethylene-tetrafluoroethylene copolymer, polyvinylidene fluoride (PVDF)), polyimide-based resin, and the like; and various elastomers such as polyurethane-based elastomer, polyester-based elastomer, polyolefin-based elastomer, polyamide-based elastomer, polystyrene-based elastomer, fluoro-based elastomer, silicone rubber, and latex rubber. In this case, a mixture of one or two or more kinds of these materials may be employed.

Among these materials, polyurethane-based elastomer, polyolefin-based elastomer and polyester-based elastomer are particularly preferred because when using these materials formation of the protruding portions 34 can be controlled easily.

The average thickness of the inner layer 31 (excluding those portions that have the protruding portions 34) is not particularly limited, but in general it should preferably be within the range of 0.05–0.8 mm, and more preferably within the range of 0.05–0.4 mm.

The outer layer 32 is constructed at the outermost peripheral side of the outer cover 3.

The outer layer 32 is preferably formed of a material having chemical resistance. By forming the outer layer 32 from such a material, the outer cover 3 will suffer very little degradation even over repeated cleaning and sterilization. As a result, there is less possibility that the outer cover 3 is hardened to reduce its flexibility or that the outer cover 3 is peeled off from the reticular tube 22 due to occurrence of crack and the like.

Further, the outer layer 32 is given a relatively high hardness. Preferably, the hardness of the outer layer 32 is higher than the hardness of the inner layer 31 and the intermediate layer 33. In this way, it will be difficult to damage the surface of the outer cover 3 even over repeated use, and this makes it difficult for cracks and the like to occur.

In the three layered structure described above, if the outer layer 32 is given a relatively high hardness in order to obtain chemical resistance and resistance to damage, there is the risk that the flexibility and resilience of the flexible tube 1a will be lowered. However, in the present invention, this risk is eliminated by the provision of the flexible intermediate layer 33 described below.

The constituent material of the outer layer 32 is not particularly limited. It is possible to use various resins having flexibility such as polyvinyl chloride, polyolefin (e.g., polyethylene, polypropylene, ethylene-vinylacetate copolymer), polyamide, polyester (e.g., polyethylene terephthalate (PET), polybutylene terephthalate), polyurethane, polystyrene resin, fluoro-based resin (e.g., polytetrafluoroethylene, ethylene-tetrafluoroethylene copolymer), polyimide, and the like; and various elastomers such as polyurethane-based elastomer, polyester-based elastomer, polyolefin-based elastomer, polyamide-based elastomer, silicone rubber, latex rubber, and the like. In this case, a mixture of one or two or more kinds of these materials may be employed.

Among these materials, polyolefin such as ethylene-vinylacetate copolymer, fluoro-based resin such as polytetrafluoroethylene, ethylene-tetrafluoroethylene copolymer and the like, polyester-based elastomer, polyolefin-based elastomer, fluorine-based elastomer, and silicone rubber are particularly preferred because they have excellent chemical resistance.

The average thickness of the outer layer 32 is not particularly limited, but it should preferably be in the range of 0.05–0.8 mm, and more preferably in the range of 0.05–0.4 mm.

The intermediate layer 33 is formed between the inner layer 31 and the outer layer 32.

The intermediate layer 33 is a more flexible layer than the outer layer 32. Further, the intermediate layer 33 is preferably a layer having excellent elasticity. In this way, the intermediate layer 33 functions as a cushioning layer between the inner layer 31 and the outer layer 32.

The cushioning function of the intermediate layer 33 will now be described in detail. Namely, when the flexible tube 1a is bent, the deformed intermediate layer 33 generates a strong restoring force because of the high resilience of the intermediate layer 33. Then, since the intermediate layer 33 is arranged between the outer layer 32 and the inner layer 31 both having relatively high hardness, the restoring force of the intermediate layer 33 is transmitted efficiently to the inner layer 31 and the outer layer 33, respectively. As a result, almost all of the restoring force of the intermediate layer 33 functions as a force for restoring the bent flexible tube 1a. Accordingly, by constructing the outer cover 3 with the laminated structure described above, it is possible to obtain a flexible tube 1a having excellent resilience.

The constituent material of the intermediate layer 33 is not particularly limited to a specific material. It is possible to use various resins having flexibility such as polyvinyl chloride, polyolefin (e.g., polyethylene, polypropylene, ethylene-vinylacetate copolymer), polyamide, polyester (e.g., polyethylene terephthalate (PET), polybutylene terephthalate), polyurethane, polystyrene resin, fluoro-based resin (e.g., polytetrafluoroethylene, ethylene-tetrafluoroethylene copolymer), polyimide, and the like; and various elastomers such as polyurethane-based elastomer, polyester-based elastomer, polyolefin-based elastomer, polyamide-based elastomer, silicone rubber, latex rubber, and the like. In this case, a mixture of one or two or more kinds of these materials may be employed.

Among these materials, low hardness polyurethane-based elastomer, polyolefin-based elastomer, and polyester-based elastomer are particularly preferred because they have excellent elasticity and resilience.

The average thickness of the intermediate layer 33 is not particularly limited, but it should preferably be in the range of 0.05–0.8 mm, and preferably in range of 0.05–0.4 mm.

Now, so long as the core member 2 and the instruments and the like passed through the inside thereof are protected against body fluids and the like, and so long as the bendability of the flexible tube 1a is not impaired, there is no specific restriction to the overall thickness of the outer cover 3 (excluding those portions that have the protruding portions 34), but normally it should preferably be in the approximate range of 0.15–0.9 mm, and more preferably in the range of 0.3–0.8 mm.

Further, in the flexible tube 1a, a plurality of easily bendable portions A are formed in a spaced apart manner (at prescribed intervals) along the longitudinal direction thereof. As will be described later, when the flexible tube 1a is being bent, these easily bendable portions A are localizedly bent at a smaller curvature radius.

In the present embodiment, such easily bendable portion A is formed at two locations. However, the present invention is not limited to this arrangement, and it is possible to provide three or more easily bendable portions A.

Further, an intermediate portion B is formed between the adjacent easily bendable portions A.

In the easily bendable portion A, the thickness of the outer layer 32 and intermediate layer 33 of the outer cover 3 are different than those in the other portions (intermediate portion B and the like) of the flexible tube 1a. Namely, the thickness of the outer layer 32 in the easily bendable portions A is thinner than the thickness of the outer layer 32 in the other portions of the flexible tube 1a, and the thickness of the intermediate layer 33 in the easily bendable portions A is thicker than the thickness of the intermediate layer 33 in the other portions of the flexible tube 1a.

In the portions of the flexible tube 1a other than the easily bendable portions A, the thickness of the outer layer 32 and the intermediate layer 33 is roughly fixed (uniform) along the longitudinal direction. Further, the thickness of the inner layer 31 is roughly fixed (uniform) along the entire length of the flexible tube 1a.

Further, the thickness of each layer of the outer cover 3 is roughly fixed in the circumferential direction.

Now, when the thickness of the thinnest portion of the outer layer 32 is defined as $T2_{min}$ and the thickness of the thickest portion of the outer layer 32 is defined as $T2_{max}$, the value of the ratio $T2_{min}/T2_{max}$ is not limited to a specific value. However, it is preferred that the value of the ratio $T2_{min}/T2_{max}$ lies in the range of 0.05–0.95, more preferably in the range of 0.1–0.6.

Further, when the thickness of the thinnest portion of the intermediate layer 33 is defined as $T3_{min}$ and the thickness of the thickest portion of the intermediate layer 33 is defined as $T3_{max}$, the value of the ratio $T3_{min}/T3_{max}$ is not limited to a specific value. However, it is preferred that the value of the ratio $T3_{min}/T3_{max}$ lies in the range of 0.05–0.95, more preferably in the range of 0.1–0.6.

By providing such structures, the outer cover 3 of the portions of the flexible tube 1a other than the easily bendable portions A has a relatively high flexural rigidity, because the portions of the flexible tube are comprised of a high proportion of the relatively hard (high rigidity) outer layer 32 and a low proportion of the relatively flexible intermediate layer 33. In contrast with this, the outer cover 3 of the easily bendable portions A has a relatively low flexural rigidity, because the outer cover 3 of the easily bendable portions A is comprised of a low proportion of the relatively hard (high rigidity) outer layer 32 and a high proportion of the relatively flexible intermediate layer 33.

Accordingly, the flexural rigidity of the outer cover 3 changes locally (becomes smaller) at the easily bendable portions A. In this way, the flexural rigidity of the entire flexible tube 1a becomes smaller at the easily bendable portions A than at the other portions. Consequently, when the flexible tube 1a is being bent, the easily bendable portions A will be bent locally with a smaller curvature radius.

Further, in the present embodiment, the thickness of the entire outer cover 3 (excluding those portions that have the protruding portions 34) is roughly fixed (uniform) along the longitudinal direction thereof. In this way, it becomes possible to roughly fix the outer diameter of the flexible tube 1a along the longitudinal direction, and this reduces the burden on the patient.

In this connection, FIG. 3 shows the overall bending state when the flexible tube 1a is bent in one direction to form a rough C-shaped (U-shaped) bend. Hereafter, this state will be referred to as the "bending state".

However, it should be noted that this "bending state" only refers to the bending state of the flexible tube 1a, and does not include the bending state of the bendable tube 5.

In this regard, it is to be noted that the easily bendable portions A can easily bend isotropically in the circumferential direction. Therefore, even in the case where the flexible tube 1a of the present embodiment is bent in any direction, the bending state will be roughly the same. However, in the present invention, it is sufficient for the bendable portion A that if the bending state described below can be obtained when the flexible tube 1a is bent in at least one direction.

When the flexible tube 1a is in the bending state, the curvature radius is smaller localizedly at each of the easily bendable portions A. As described above, a plurality of these easily bendable portions A are formed in a spaced apart manner (at prescribed intervals) along the longitudinal direction of the flexible tube 1a. Hereafter, the curvature radius of the flexible tube 1a will refer to the curvature radius at a center line (axial line) 20.

When an overall observation of the bending state of the flexible tube 1a is carried out visually, the flexible tube 1a is observed, in an exaggerated sense, to be bent through an obtuse angle at corners formed at the easily bendable portions A (see FIG. 3).

On the other hand, the portions of the flexible tube 1a other than the easily bendable portions A (that is, the intermediate portion B and the like) is relatively gently bent in the bending state as compared with the easily bendable portions A.

In the bending state, when the average of the curvature radius (having a length shown by $r_1$ in FIG. 3) of each easily bendable portion A is defined as $R_1$ and the curvature radius (or the average thereof) of the center portion (i. e., the center portion of the intermediate portion B) lying between the adjacent easily bendable portions A is defined as $R_2$, then the preferred value of the ratio $R_1/R_2$ will be different depending on such factors as the type of endoscope, the intended use, the number of easily bendable portions A and the like, but normally such ratio is preferably in the range of 0.2–0.9, and more preferably in the range of 0.4–0.8. When the ratio $R_1/R_2$ lies in such range, the frictional force with the inner walls of the body cavity can be further reduced, and this makes it possible to further improve the insertion operability. In this regard, the curvature radius $r_1$ of each easily bendable portion A can represent, for example, the curvature radius at the center portion of each easily bendable portion A.

The preferred value of the interval (or the average thereof) between the adjacent easily bendable portions A indicated with $L_1$ in FIG. 3 will be different depending on such factors as the type of endoscope, the intended use, the number of easily bendable portions A and the like, but normally the length $L_1$ is preferably in the range of 50–400 mm, and more preferably in the range of 70–300 mm. When the length $L_1$ lies in such range, the bending state of the flexible tube 1a inserted into a body cavity will have even better matchability with the shape of the body cavity, and this will further improve the insertion operability.

The preferred value of the length of each easily bendable portion A (i.e., the length $L_2$ shown in FIG. 3) will be different depending on such factors as the type of endoscope, the intended use, the number of easily bendable portions A and the like, but normally the length $L_2$ is preferably in the range of 10–50 mm, and more preferably in the range of 15–40 mm.

Further, the length of the portion that runs from the tip end 11 to the closest easily bendable portion A (i.e., the length $L_3$ shown in FIG. 3), and the length of the portion that runs from the base end 12 to the closest easily bendable portion A (i.e., the length $L_4$ shown in FIG. 3) do not have any specific restrictions, but it is possible, for example, to make the lengths $L_3$ and $L_4$ roughly the same as the length $L_1$.

Next, the operation (i.e., the insertion state into a body cavity) of the flexible tube 1a will be described.

FIG. 4 shows the state in which the flexible tube 1a is being inserted into the inside of a tubular cavity (model) 90 having a U-shaped internal space and in this state a push-in force is applied to the base end of the flexible tube 1a for advancing the flexible tube 1a deeper into the interior of the tubular cavity 90. In contrast, FIG. 8 shows an insertion state of a prior art flexible tube 100 during insertion into a tubular cavity in the same way as described above.

First, for the purpose of comparison, the insertion state of the prior art flexible tube 100 inserted into the tubular cavity 90 will be described with reference to FIG. 8.

Figure 8:
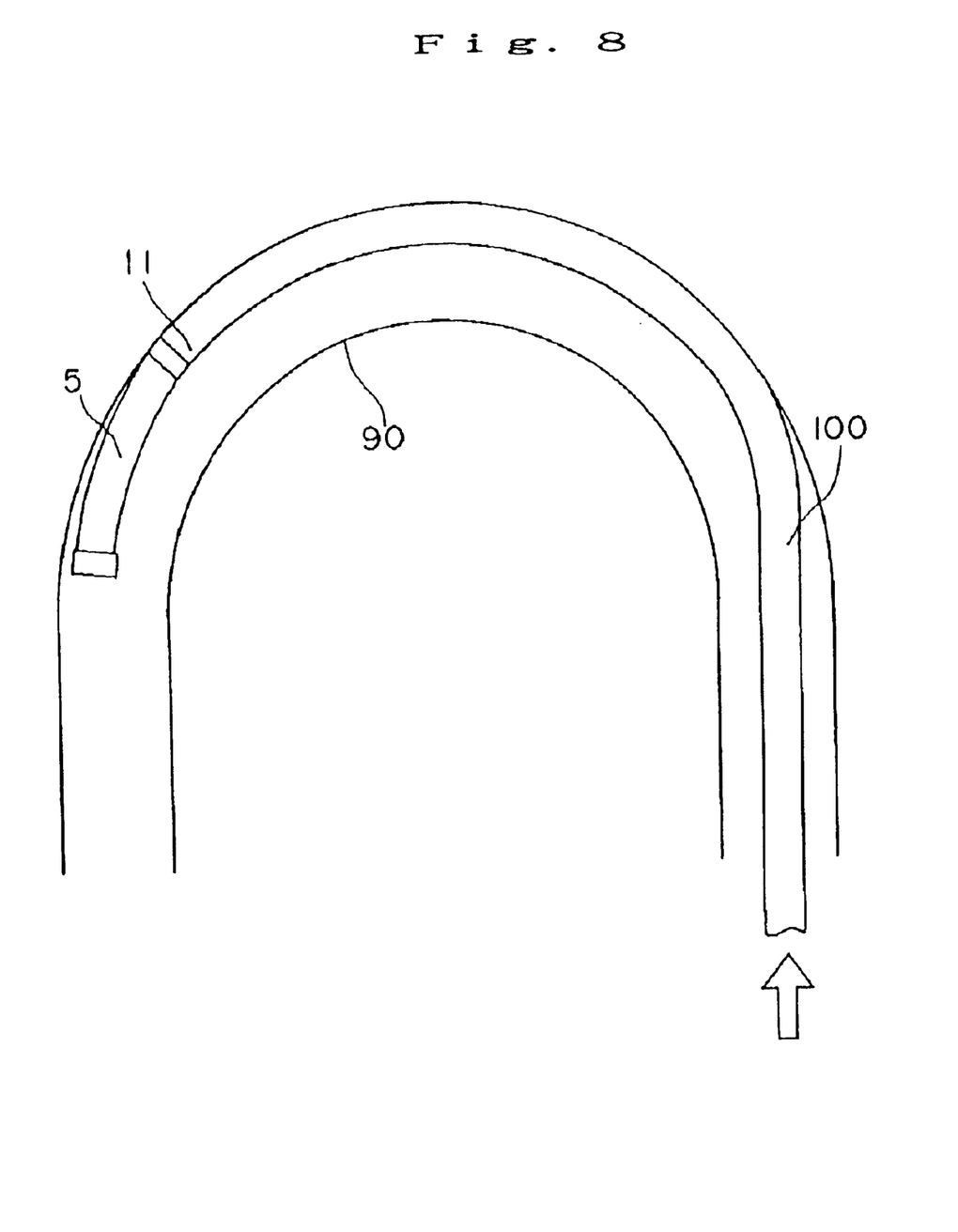
FIG. 8 is an illustration showing the state that a prior art flexible tube is inserted into a tubular cavity.

In the situation shown in FIG. 8, when a push-in force is applied to the base side of the flexible tube 100, the outer curved portion of the flexible tube 100 bending along the tubular cavity 90 pushes against the inner wall of the tubular cavity 90. At this time, because roughly all of the prior art flexible tube 100 bends in a uniform manner, a large portion of the outer curved portion of the flexible tube 100 is in contact with the inner wall of the tubular cavity 90. Consequently, the contact area with the inner wall of the tubular cavity 90 is quite large, and this results in a large resistance (frictional force) received from the inner wall of the tubular cavity 90, so that it is difficult to advance the flexible tube 100 deep into the interior of the tubular cavity 90. Accordingly, the insertion operability of the prior art flexible tube 100 is poor.

In contrast with this, according to the present invention, as shown in FIG. 4, only the easily bendable portions A (or portions in the vicinity thereof) of the flexible tube 1*a* are in contact with the inner wall of the tubular cavity 90. Further, even when the portions of the flexible tube 1*a* other than the easily bendable portions A are in contact with the inner wall of the tubular cavity 90, the push-in force against the inner wall of the tubular cavity 90 is small. Therefore, because the resistance (frictional force) received from the inner wall of the tubular cavity 90 is small, the flexible tube 1*a* can be easily advanced (moved) deep into the interior of the tubular cavity 90. Accordingly, the flexible tube 1*a* of the present invention has excellent insertion operability.

Further, in comparison with the prior art flexible tube 100, because the flexible tube 1*a* of the present invention will have a small contact area with the inner walls of a body cavity, the pressure felt by the patient will be reduced, and this makes it possible to reduce the burden on the patient.

In this regard, even though this type of flexible tube 1*a* is especially suited for use as a flexible tube for an endoscope used as a large intestine scope, the present invention is not limited to such application, and it is possible to use the flexible tube 1*a* as a flexible tube for other various endoscopes used in various applications.

In the embodiment of the flexible tube 1*a* described above, the thickness of each layer of the outer cover 3 at the easily bendable portions A, and the thickness of each layer of the outer cover 3 at the other portions of the flexible tube 1*a* are fixed (uniform) along the longitudinal direction thereof, respectively. However, it should be noted that the present invention is not limited to this structure, and it is also possible to provide a structure where the thickness of each layer changes along the longitudinal direction. Further, it is also possible to provide a structure where the overall thickness of the outer cover 3 changes along the longitudinal direction thereof. For example, when adopting such a structure, the flexural rigidity of the flexible tube 1*a* is at the portions other than the easily bendable portions A can be increased in the direction toward the base end 12.

Further, even though the outer cover 3 in the present embodiment was described as including the single intermediate layer 33, it is also possible to provide two or more intermediate layers 33.

Further, even though in the present embodiment described above the entire of the outer cover 3 was constructed to have the laminated structure, only one or more portions of the outer cover may be formed into such laminated structure.

Now, even though there are no specific restrictions regarding the method of manufacturing the flexible tube 1*a* described above. For example, if the outer cover 3 is applied over the core body 2 using an extrusion molding method, it is possible to manufacture the flexible tube 1*a* in a continuous manner. Further, by simultaneously extruding the inner layer 31, outer layer 32 and intermediate layer 33 with an extrusion molding machine equipped with a plurality of extrusion openings, it is possible to cover the core body 2 with an outer cover 3 having a laminated structure. Further, by adjusting the pulling speed of the core body 2 and the discharge quantity (i.e., the quantity of material discharged per unit time) of the constituent material of each layer extruded through each extrusion opening, it is possible to control the thickness of each layer.

As for the temperature of the material during extrusion, there are no specific restrictions, but a preferred example of an approximate range would be 130–220° C., with the approximate range of 165–205° C. being even more preferred. In the case where the temperature of the material during extrusion is within such range, the material will have excellent formability for the outer cover 3. Consequently, it becomes possible to improve the uniformity of the thickness of the outer cover 3.

However, in the case where the main component of the construction material of the outer cover 3 is a rubber compound such as silicone rubber or the like, the heat generated during kneading will degrade the plasticity of the construction material of the outer cover 3. Accordingly, in such case, kneading is preferably carried out at a temperature within the approximate range of 10–70° C.

Figure 5:
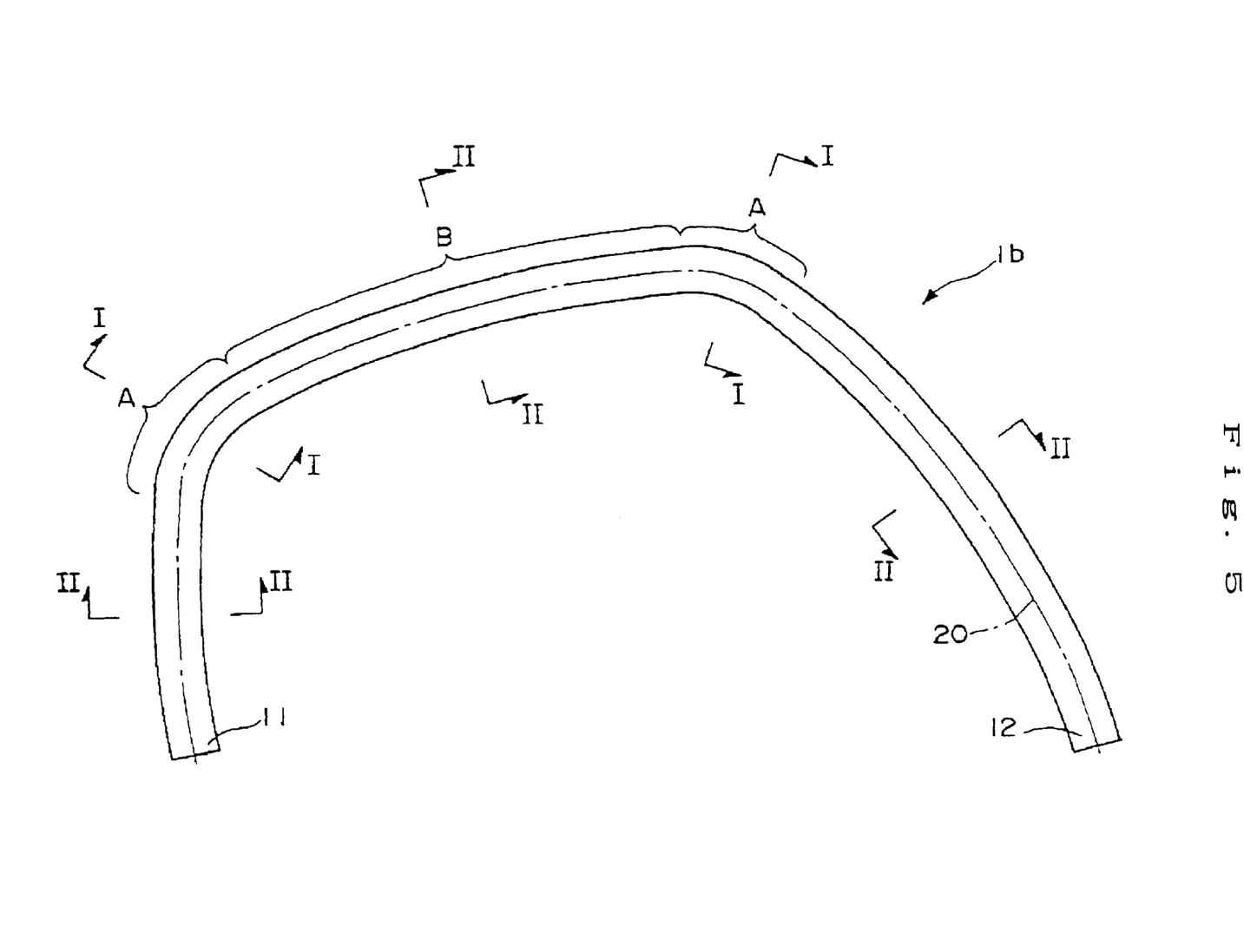
FIG. 5 is an illustration showing the state that a flexible tube for an endoscope of a second embodiment in accordance with the present invention is being bent.
Figure 6:
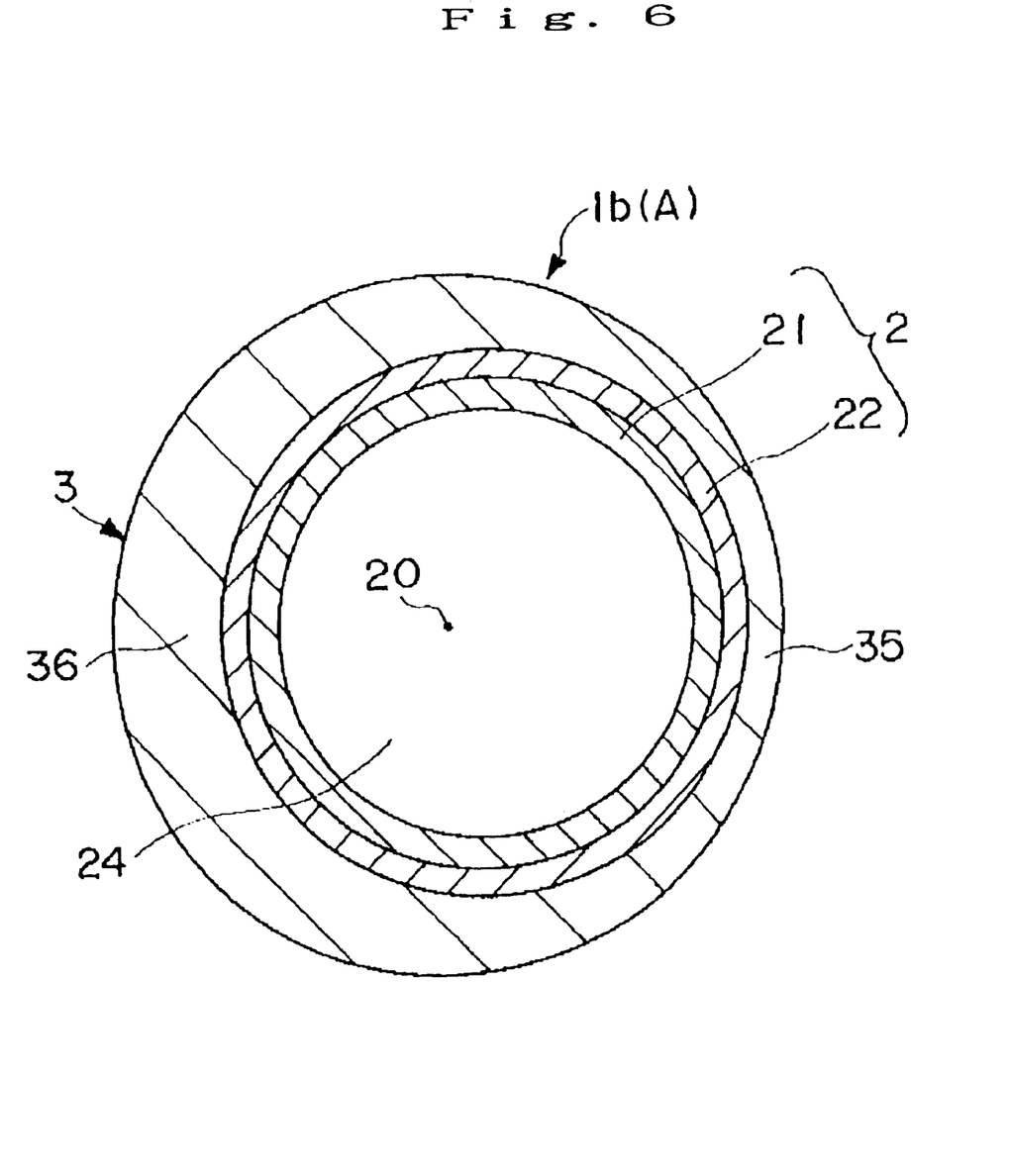
FIG. 6 is a cross-sectional view taken along the I—I line in FIG. 5.
Figure 7:
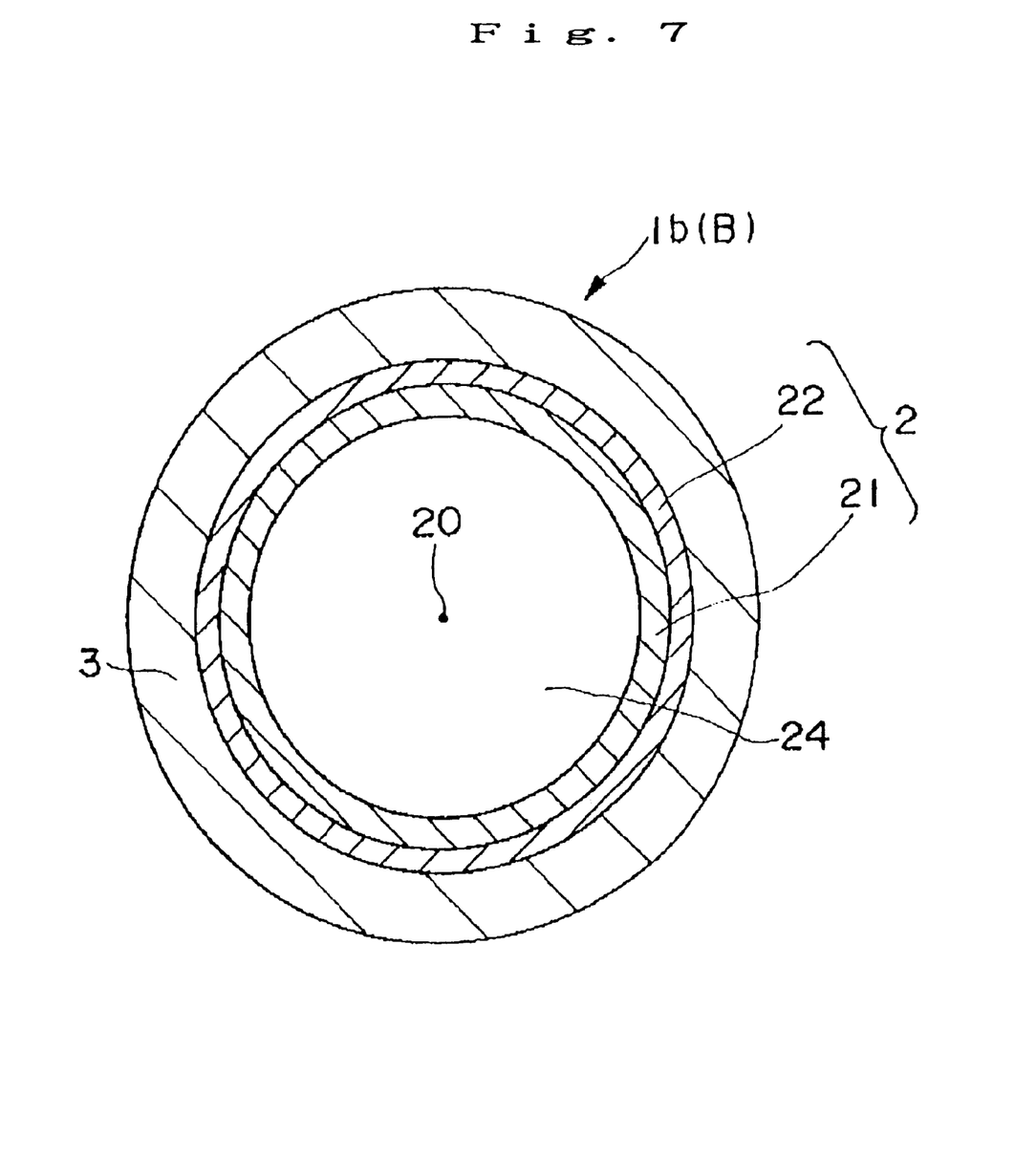
FIG. 7 is a cross-sectional view taken along the II—II line in FIG. 6.

Next, FIG. 5 is an illustration showing a second embodiment of a flexible tube for an endoscope of the present invention, FIG. 6 is a cross-sectional view taken along the arrows I—I in FIG. 5, and FIG. 7 is a cross-sectional view taken along the arrows II—II in FIG. 5. Hereafter, the second embodiment of a flexible tube for an endoscope of the present invention will be described with reference to FIGS. 5–7, but it should be noted that this description will focus on elements that are different from those described above in the first embodiment, and therefore a description of the same elements will be omitted.

Namely, the outer cover 3 of the flexible tube 1*b* of this second embodiment is different from the outer cover 3 of the flexible tube 1*a* of the first embodiment in the structure thereof.

As shown in FIG. 6 and FIG. 7, the outer cover 3 of the flexible tube 1*b* is formed into a single layer structure.

There are no specific restrictions for the constituent material of this type of outer cover 3, and it is possible, for example, to construct this outer cover 3 using the same material described above for the flexible tube 1*a* of the first embodiment. Further, there are no specific restrictions for the average thickness of the outer cover 3 (excluding those portions provided with the protruding portions 34), and it is possible, for example, for the outer cover 3 of the present embodiment to have the same average thickness as the outer cover 3 of the flexible tube 1*a* of the first embodiment.

As shown in FIG. 7, the thickness of the outer cover 3 at the portions (intermediate portion B and the like) of the flexible tube 1*b* other than the easily bendable portions A is roughly fixed (uniform) along the circumferential direction (over the entire circumference).

In contrast with this, as shown in FIG. 6, the thickness of the outer cover 3 at the easily bendable portions A changes along the circumferential direction. Namely, at each of the easily bendable portions A, the outer cover 3 includes a thin portion 35 where the thickness of the outer cover 3 is relatively thin, and a thick portion 36 where the thickness of the outer cover 3 is relatively thick. More specifically, the thickness of the thin portion 35 is thinner than the thickness of the outer cover 3 at the portions of the flexible tube 1*b* other than the easily bendable portions A, and the thickness of the thick portion 36 is thicker than the thickness of the outer cover 3 at the portions of the flexible tube 1*b* other than the easily bendable portions A.

The thin portion 35 and the thick portion 36 are formed at positions opposite each other with respect to the center line 20. Further, at each of the easily bendable portions A, the thin portion 35 and the thick portion 36 are formed in the same circumferential position.

By constructing the outer cover 3 in the way, the flexural rigidity of the outer cover 3 at each of the easily bendable portions A is smaller than the flexural rigidity of the outer cover 3 at the portions of the flexible tube 1b other than the easily bendable portions A when the easily bendable portion A is bent in a direction where the thin portion 35 forms an inside curve. Conversely, the flexural rigidity of the outer cover 3 at each of the easily bendable portions A is greater than the flexural rigidity of the outer cover 3 at the portions of the flexible tube 1b other than the easily bendable portions A when the easily bendable portion A is bent in a direction where the thick portion 36 forms an inside curve.

Further, by making the flexural rigidity of the outer cover 3 change locally in the manner described above, the overall flexural rigidity of the flexible tube 1b is smaller than the flexural rigidity of the portions of the flexible tube 1b other than the easily bendable portions A when the flexible tube 1b is bent in a direction where each thin portion 35 forms an inside curve. Conversely, the overall flexural rigidity of the flexible tube 1b is greater than the flexural rigidity of the portions of the flexible tube 1b other than the easily bendable portions A when the flexible tube 1b is bent in a direction where each thick portion 36 forms an inside curve.

Furthermore, in the above example, the thickness of the outer cover at each of the easily bendable portions A and the thickness of the outer cover at each of the intermediate portions B are changed as shown in FIG. 6 and FIG. 7. However, it is possible to form the outer cover so that its thickness is gradually changed or is changed in a step manner in each of the transition portions between each of the easily bendable portions A and each of the intermediate portions B.

According to the above structures, each of the easily bendable portions A will have a relatively small curvature radius when the thin portion 35 forms an inside curve, and a relatively large curvature radius when the thick portion 36 forms an inside curve. Accordingly, when the flexible tube 1b is bent in a direction where each thin portion 35 forms an inside curve, the local curvature radius at each of the easily bendable portions A will be small, and as shown in FIG. 5, this makes it possible to obtain the same bending state described above for the flexible tube 1a of the first embodiment. In this bending state, the values of $R_1/R_2$, $L_1$ and the like are preferably in the same ranges described above for the flexible tube 1a of the first embodiment.

Accordingly, in the present embodiment, the easily bendable portions A are bendable anisotropically.

In this regard, it should be understood that the present invention includes such a flexible tube 1b as the second embodiment in which the bending state described above can be obtained by bending the flexible tube 1b in a specific direction, as opposed to the first embodiment where such bending state was obtained for all directions. The reason for this is as follows. Namely, there are cases where the bending direction of the flexible tube 1b is predetermined to be roughly one fixed direction in accordance with the type and intended use of the endoscope. Accordingly, by connecting the flexible tube 1b to the operating section 6 in such a way that each of the thin portions 35 forms an inside curve to match such predetermined bending direction, it is possible to obtain the same results obtained by the flexible tube 1a of the first embodiment.

Furthermore, because the flexible tube 1b of the second embodiment will be relatively difficult to bend in directions other than the predetermined direction, the push-in force applied to the base end will be transmitted more reliably to the tip end, and this further improves the insertion operability.

Further, in the above example, each of the portions of the outside curves of the easily bendable portions A pushes against the inner wall of the tubular cavity through the thick portion 36 where the thickness of the outer cover 3 is relatively thick, so that the thick portion 36 acts as a cushioning means. As a result, the adverse effect felt by the inner walls of the tubular cavity are reduced, and this makes it possible to further improve safety (see FIG. 4).

In this second embodiment, a description was made with regard to the case where the easily bendable direction of each easily bendable portion A is the same. However, the present invention is not limited to such arrangement, and by changing the circumferential positions of the thin portions 35 and thick portions 36 at the easily bendable portions A, each easily bendable portion A can be given a different easily bendable direction. By providing this type of arrangement, each easily bendable portion A can be given a small curvature radius when the flexible tube 1b is bent, for example, in an S-shape manner, in three dimensions or the like. In this way, it is possible to form easily bendable portions A to match various different bending directions in accordance with different insertion locations (regions), and this results in a high degree of design freedom.

There are no specific restrictions regarding the method of manufacturing the flexible tube 1b described above, and it is possible, for example, to cover the core body 2 with the outer cover 3 using the extrusion molding method described above in the first embodiment. For example, in such case, by decentering (shifting) the central axis of the die (extrusion opening) of the extrusion machine from the central axis of the core body 2 at the regions where the easily bendable portions A are to be formed, it is possible to form the thin portion 35 and the thick portion 36 described above.

In addition, it should be also noted that the present invention is not limited to the structure having the thin portion 35 and thick portion 36 shown in the drawings. For example, the core body 2 can be covered with an outer cover 3 having an elliptical cross section. In such case, the cross section of the outer cover 3 will show two thin portions and two thick portions located respectively at opposing 180° positions. Namely, each thin portion and each thick portion are located at 90° (central angle) shifting positions with respect to each other. Accordingly, when the easily bendable portion formed with such thin portions and thick portions is bent in the two directions where each thin portion forms an inside curve, the curvature radius thereof will become small, but when bending is carried out in the two directions shifted 90° thereto (i.e., in the two directions where each thick portion forms an inside curve), the curvature radius will not become small.

Further, in the present embodiment, even though the outer cover 3 was described as being formed into a single layer structure, it is also possible for the outer cover 3 to be formed into a laminated structure having a plurality of layers.

At this point it should be noted that the present invention is not limited to the specific embodiments of a flexible tube for an endoscope described above, and so long as the same functions are achieved, it is possible to make various changes and additions to each portion of the flexible tube for an endoscope of the present invention.

Namely, the flexible tube for an endoscope of the present invention is not limited to the structures shown in the drawings, and it is possible to use any other structure that makes it possible to obtain the bending state described above when the flexible tube is bent in at least one direction. For example, by changing (replacing) the thickness, presence or absence, and constituent material of each layer forming the outer cover 3 at each of the easily bendable portions A (or at portions lying before and after such easily bendable portions A), it is also possible to obtain the bending state described above.

Further, instead of changing the structure of the outer cover 3 along the longitudinal direction, it is also possible to form the easily bendable portions A by changing the structure of the core body 2 along the longitudinal direction thereof. For example, the easily bendable portions A can be formed by the following methods:

The winding pitch of the coil 21 can be increased locally at positions corresponding to the easily bendable portions A (or at positions corresponding to the portions lying before and after such easily bendable portions A).

The width and/or thickness of the band-shaped material used to make the coil 21 can be reduced locally at positions corresponding to the easily bendable portions A (or at positions corresponding to the portions lying before and after such easily bendable portions A).

It is also possible, of course, to use any combination of the methods described above as well as other methods.

As described above, because the present invention makes it possible to reduce the resistance that the flexible tube for an endoscope receives from the inner walls of a body cavity, it becomes possible to easily insert the flexible tube for an endoscope deep into the interior of the body cavity. Accordingly, the flexible tube for an endoscope of the present invention has excellent insertion operability.

Further, in the case where easily bendable portions are formed by locally changing the flexural rigidity of the outer cover, it becomes possible to achieve the above-described results with a simple structure, and this in turn makes it possible to easily manufacture the flexible tube for an endoscope of the present invention at low cost.

Finally, it is to be understood that many changes and additions may be made to the embodiments described above without departing from the scope and spirit of the invention as defined in the following claims.

Further, it is also to be understood that the present disclosure relates to subject matter contained in Japanese Patent Application No. 2000-265847 (filed on Sep. 1, 2000) which is expressly incorporated herein by reference in its entirety.

What is claimed is:

1. A flexible tube for an endoscope, comprising:
   an elongated flexible tubular body; and
   a plurality of easily bendable portions provided in the tubular body in a spaced apart manner along the longitudinal direction thereof, each of these easily bendable portions being adapted to be bent locally with a curvature radius smaller than other portions of the tubular body when the flexible tube is bent in one specified direction.

2. The flexible tube for an endoscope as claimed in claim 1, wherein the average interval between the adjacent easily bendable portions is in the range 50–400 mm.

3. The flexible tube for an endoscope as claimed in claim 1, wherein when the average of the curvature radius of each of said easily bendable portions is defined as $R_1$ and the curvature radius of a center portion lying between said adjacent easily bendable portions is defined as $R_2$, the value of the ratio $R_1/R_2$ in the bending state lies in the range of 0.2–0.9.

4. The flexible tube for an endoscope as claimed in claim 1, wherein the flexible tubular body includes a core body having a hollow space and an outer cover which is provided over the outer periphery of the core body, the outer cover being formed into either of a single layer structure or a laminated structure having a plurality of layers.

5. The flexible tube for an endoscope as claimed in claim 4, wherein each of said easily bendable portions is formed by locally changing the flexural rigidity of the outer cover.

6. The flexible tube for an endoscope as claimed in claim 4, wherein at least one of said easily bendable portions is formed by changing the thickness of at least one layer of the laminated structure of the outer cover at a position corresponding to the easily bendable portion.

7. The flexible tube for an endoscope as claimed in claim 4, wherein the outer cover has a portion which is made of a material including at least one kind of material selected from the group consisting of polyurethane-based elastomer, polyester-based elastomer, polyolefin-based elastomer, polystyrene-based elastomer, polyamide-based elastomer, and fluoro-based elastomer.

8. The flexible tube for an endoscope as claimed in claim 4, wherein the outer cover is applied over the core body using an extrusion molding method.

9. The flexible tube for an endoscope as claimed in claim 4, wherein the core body includes a coil formed by winding a band-shaped material into a spiral and a braided tube provided over the outer periphery of the coil and formed by braiding fine wires.

10. The flexible tube for an endoscope as claimed in claim 4, wherein at least one of said easily bendable portions is formed by reducing the width and/or thickness of the band-shaped material of the coil locally at a position corresponding to the easily bendable portion.

11. A flexible tube for an endoscope, comprising:
    an elongated flexible tubular body; and
    a plurality of easily bendable portions provided in the tubular body in a spaced apart manner along the longitudinal direction thereof, each of these easily bendable portions being adapted to be bent locally with a curvature radius smaller than other portions of the tubular body when the flexible tube is bent;
    wherein the flexible tubular body includes a core body having a hollow space and an outer cover which is provided over the outer periphery of the core body, the outer cover being formed into either of a single layer structure or a laminated structure having a plurality of layers; and
    wherein at least one of said easily bendable portions is constructed from a portion of the outer cover where the thickness of the outer cover changes along the circumferential direction.

12. A flexible tube for an endoscope, comprising:
    an elongated flexible tubular body; and
    a plurality of easily bendable portions provided in the tubular body in a spaced apart manner along the longitudinal direction thereof, each of these easily bendable portions being adapted to be bent locally with a curvature radius smaller than other portions of the tubular body when the flexible tube is bent;
    wherein the flexible tubular body includes a core body having a hollow space and an outer cover which is provided over the outer periphery of the core body, the outer cover being formed into either of a single layer structure or a laminated structure having a plurality of layers; and wherein at least one of said easily bendable portions is formed by forming the outer cover so at to have an elliptical cross section at a position corresponding to the easily bendable portion.

13. A flexible tube for an endoscope, comprising:

an elongated flexible tubular body; and a plurality of easily bendable portions provided in the tubular body in a spaced apart manner along the longitudinal direction thereof, each of these easily bendable portions being adapted to be bent locally with a curvature radius smaller than other portions of the tubular body when the flexible tube is bent;

wherein the flexible tubular body includes a core body having a hollow space and an outer cover which is provided over the outer periphery of the core body, the outer cover being formed into either of a single layer structure or a laminated structure having a plurality of layers; and wherein at least on of said easily bendable portions is formed by increasing the winding pitch of the coil locally at a position corresponding to the easily bendable portion.

14. An electronic endoscope, comprising:

an operation section which is adapted to be operated by an operator; and a flexible tube for an endoscope which is connected to the operation section, the flexible tube including an elongated flexible tubular body and a plurality of easily bendable portions provided in the tubular body in a spaced apart manner along the longitudinal direction thereof, each of these easily bendable portions being adapted to bend locally with a curvature radius smaller than other portions of the tubular body when the flexible tube is bent in one specified direction.

15. A flexible tube for an endoscope, comprising:

an elongated flexible tubular body; and a plurality of easily bendable portions provided in the tubular body in a spaced apart manner along the longitudinal direction thereof, each of these easily bendable portions being adapted to be bent locally with a curvature radius smaller than other portions of the tubular body when the flexible tube is bent;

wherein the average interval between the adjacent easily bendable portions is in the range 50–400 mm.

16. A flexible tube for an endoscope, comprising:

an elongated flexible tubular body; and a plurality of easily bendable portions provided in the tubular body in a spaced apart manner along the longitudinal direction thereof, each of these easily bendable portions being adapted to be bent locally with a curvature radius smaller than other portions of the tubular body when the flexible tube is bent;

wherein when the average of the curvature radius of each of said easily bendable portions is defined as $R_1$ and the curvature radius of a center portion lying between said adjacent easily bendable portions is defined as $R_2$, the value of the ratio $R_1/R_2$ in the bending state lies in the range of 0.2–0.9.

* * * * *